US011246478B2

United States Patent
Morimoto et al.

(10) Patent No.: US 11,246,478 B2
(45) Date of Patent: Feb. 15, 2022

(54) ENDOSCOPE

(71) Applicant: FUJIFILM Corporation, Tokyo (JP)

(72) Inventors: Yasuhiko Morimoto, Kanagawa (JP); Shozo Iyama, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 762 days.

(21) Appl. No.: 15/871,890

(22) Filed: Jan. 15, 2018

(65) Prior Publication Data

US 2018/0235453 A1 Aug. 23, 2018

(30) Foreign Application Priority Data

Feb. 23, 2017 (JP) .............................. JP2017-032089

(51) Int. Cl.
| | | |
|---|---|---|
| *A61B 1/00* | (2006.01) | |
| *A61B 1/12* | (2006.01) | |
| *A61B 1/018* | (2006.01) | |
| *A61B 8/12* | (2006.01) | |
| *A61B 1/04* | (2006.01) | |
| *A61B 8/00* | (2006.01) | |

(52) U.S. Cl.
CPC .......... *A61B 1/126* (2013.01); *A61B 1/00091* (2013.01); *A61B 1/00098* (2013.01); *A61B 1/00179* (2013.01); *A61B 1/018* (2013.01); *A61B 1/04* (2013.01); *A61B 8/12* (2013.01); *A61B 8/445* (2013.01); *A61B 8/4405* (2013.01)

(58) Field of Classification Search
CPC .... A61B 1/00098; A61B 1/00091; A61B 8/12
See application file for complete search history.

(56) References Cited

U.S. PATENT DOCUMENTS

| | | | |
|---|---|---|---|
| 7,914,441 B2 | 3/2011 | Otawara | |
| 8,777,845 B2 | 7/2014 | Ikeda et al. | |
| 9,380,996 B2 | 7/2016 | Hiraoka | |
| 9,521,948 B2 | 12/2016 | Ikeda et al. | |

(Continued)

FOREIGN PATENT DOCUMENTS

| | | |
|---|---|---|
| CN | 1976620 | 6/2007 |
| CN | 103549936 | 2/2014 |

(Continued)

OTHER PUBLICATIONS

"Office Action of China Counterpart Application", dated Jul. 5, 2021, with English translation thereof, pp. 1-15.

*Primary Examiner* — Alexandra L Newton

(74) *Attorney, Agent, or Firm* — JCIPRNET

(57) ABSTRACT

An endoscope includes an insertion part that includes a distal end and a proximal end, a distal-end-portion body that is provided on a distal end side of the insertion part, and an ultrasound transducer that is provided on a distal end side of the distal-end-portion body. The distal-end-portion body includes a pair of walls, a standing base that is disposed in a space formed by the pair of walls and connected to a treatment tool outlet, an observation window that is disposed on one wall of the pair of walls, and a nozzle that is provided on the flat surface opposite to the space across the observation window and ejects washing water to the observation window. The wall surface of the other wall of the pair of walls is positioned on an extension of an ejection direction of the washing water to be ejected from the nozzle.

20 Claims, 10 Drawing Sheets

(56) References Cited

U.S. PATENT DOCUMENTS

| | | |
|---|---|---|
| 9,675,234 B2 | 6/2017 | Tsumaru et al. |
| 10,149,604 B2 | 12/2018 | Hiraoka et al. |
| 10,398,288 B2 | 9/2019 | Morimoto |
| 10,441,151 B2 | 10/2019 | Ikeda et al. |
| 10,485,403 B2 | 11/2019 | Morimoto |
| 10,492,663 B2 | 12/2019 | Hosogoe |
| 11,064,876 B2 | 7/2021 | Ikeda et al. |
| 2005/0222493 A1* | 10/2005 | Kohno ............... A61B 1/00098 600/107 |
| 2005/0228289 A1* | 10/2005 | Kohno .................... A61B 8/14 600/463 |
| 2013/0158410 A1* | 6/2013 | Ohgishi ............ A61B 1/00177 600/462 |
| 2015/0173711 A1 | 6/2015 | Hiraoka |
| 2016/0206180 A1 | 7/2016 | Hosogoe |
| 2016/0270635 A1 | 9/2016 | Tanaka et al. |
| 2016/0270637 A1 | 9/2016 | Tanaka et al. |
| 2017/0000317 A1 | 1/2017 | Iizuka |
| 2017/0014099 A1 | 1/2017 | Morimoto |
| 2020/0000429 A1 | 1/2020 | Morimoto |

FOREIGN PATENT DOCUMENTS

| | | |
|---|---|---|
| CN | 104720733 | 6/2015 |
| CN | 105455853 | 4/2016 |
| CN | 105592768 | 5/2016 |
| CN | 105596028 | 5/2016 |
| CN | 105916428 | 8/2016 |
| CN | 105982635 | 10/2016 |
| CN | 106132312 | 11/2016 |
| EP | 2886037 | 6/2015 |
| JP | H0235701 | 3/1990 |
| JP | 2001029312 | 2/2001 |
| JP | 2012045327 | 3/2012 |
| WO | 2014038638 | 3/2014 |
| WO | 2016199694 | 12/2016 |

* cited by examiner

ENDOSCOPE

CROSS-REFERENCE TO RELATED APPLICATIONS

The present application claims priority under 35 U.S.C. § 119 to Japanese Patent Application No. 2017-032089, filed on Feb. 23, 2017. Each of the above application(s) is hereby expressly incorporated by reference, in its entirety, into the present application.

BACKGROUND OF THE INVENTION

1. Field of the Invention

The present invention relates to an endoscope that includes ultrasound transducers.

2. Description of the Related Art

For example, an ultrasonic endoscope and a duodenoscope are known as endoscopes that include a standing base adjusting the protruding angle of a treatment tool. A procedure, such as fine needle aspiration cytology (FNA), is performed using an ultrasonic endoscope. A procedure, such as endoscopic retrograde cholangiopancreatography (ERCP), is performed using a duodenoscope.

While the procedure using the ultrasonic endoscope is performed, mucus and blood may adhere to an observation window that is provided at a distal end portion of an insertion part of an endoscope. WO2014/038638A discloses an ultrasonic endoscope that ejects washing water to the surface of the observation window from a nozzle.

SUMMARY OF THE INVENTION

Incidentally, while the procedure, such as FNA, is performed using the ultrasonic endoscope, mucus, blood, and a contrast medium may adhere to the periphery of the standing base. For example, in a case in which a procedure time is long, mucus, blood, and the like adhering to the periphery of the standing base are fixed. For this reason, there is a problem that the operating resistance of the standing base is made larger than that in an initial state.

Since washing water is ejected toward the observation window from the nozzle in the ultrasonic endoscope disclosed in WO2014/038638A, it is difficult to reliably wash the periphery of the standing base.

The invention has been made in consideration of the above-mentioned circumstances, and an object of the invention is to provide an endoscope of which a standing base provided at a distal end portion of the endoscope can be washed.

An endoscope according to a first aspect includes an insertion part that includes a distal end and a proximal end, a distal-end-portion body that is provided on a distal end side of the insertion part and formed with a treatment tool outlet from which a treatment tool is led out, and an ultrasound transducer that is provided on a distal end side of the distal-end-portion body. The distal-end-portion body includes a pair of walls that includes wall surfaces facing each other, a standing base that is disposed in a space formed by the pair of walls and connected to the treatment tool outlet and that is rotationally moved between a standing position and a falling position, an observation window that is disposed on a flat surface inclined with respect to an axial direction of the distal-end-portion body on the distal end side of one wall of the pair of walls, a nozzle that is provided on the flat surface opposite to the space across the observation window and ejects washing water to the observation window, and a fluid pipe line that is connected to the nozzle. The wall surface of the other wall of the pair of walls is positioned on an extension of an ejection direction of the washing water to be ejected from the nozzle.

According to a second aspect, in the endoscope, the ejection direction of the washing water to be ejected from the nozzle is a direction crossing the axial direction of the distal-end-portion body.

According to a third aspect, in the endoscope, the nozzle is disposed on the distal end side of the distal-end-portion body and the observation window is disposed closer to a proximal end of the distal-end-portion body than the nozzle.

According to a fourth aspect, in the endoscope, the nozzle is disposed closer to an outer periphery of the distal-end-portion body than the observation window.

According to a fifth aspect, in the endoscope, the wall surface of the other wall of the pair of walls is longer than the wall surface of the one wall in the axial direction of the distal-end-portion body, and a distal end of the wall surface of the other wall is disposed closer to the distal end side of the distal-end-portion body than a distal end of the wall surface of one wall.

According to a sixth aspect, in the endoscope, the flat surface is inclined toward the space.

According to a seventh aspect, in the endoscope, one wall includes an inclined surface inclining from the flat surface toward the space.

According to an eighth aspect, in the endoscope, the observation window is disposed in a recessed portion provided on the flat surface.

According to a ninth aspect, the endoscope further includes a port that is provided on the wall surface of the one wall and ejects the washing water, and a branch pipe line that connects the port to the fluid pipe line.

According to a tenth aspect, in the endoscope, the wall surface of the other wall is positioned on an extension of the ejection direction of the washing water to be ejected from the port in a state in which the standing base is in the falling position.

According to the invention, the periphery of a standing base of an endoscope including an ultrasound transducer can be washed.

DESCRIPTION OF THE PREFERRED EMBODIMENTS

Preferred embodiments of the invention will be described below with reference to the accompanying drawings. The invention will be described using the following preferred embodiments. The invention can be modified by various methods without departing from the scope of the invention, and the embodiments other than the embodiments can be used. Accordingly, all modifications within the scope of the invention are included in the claims.

First Embodiment

Figure 1:
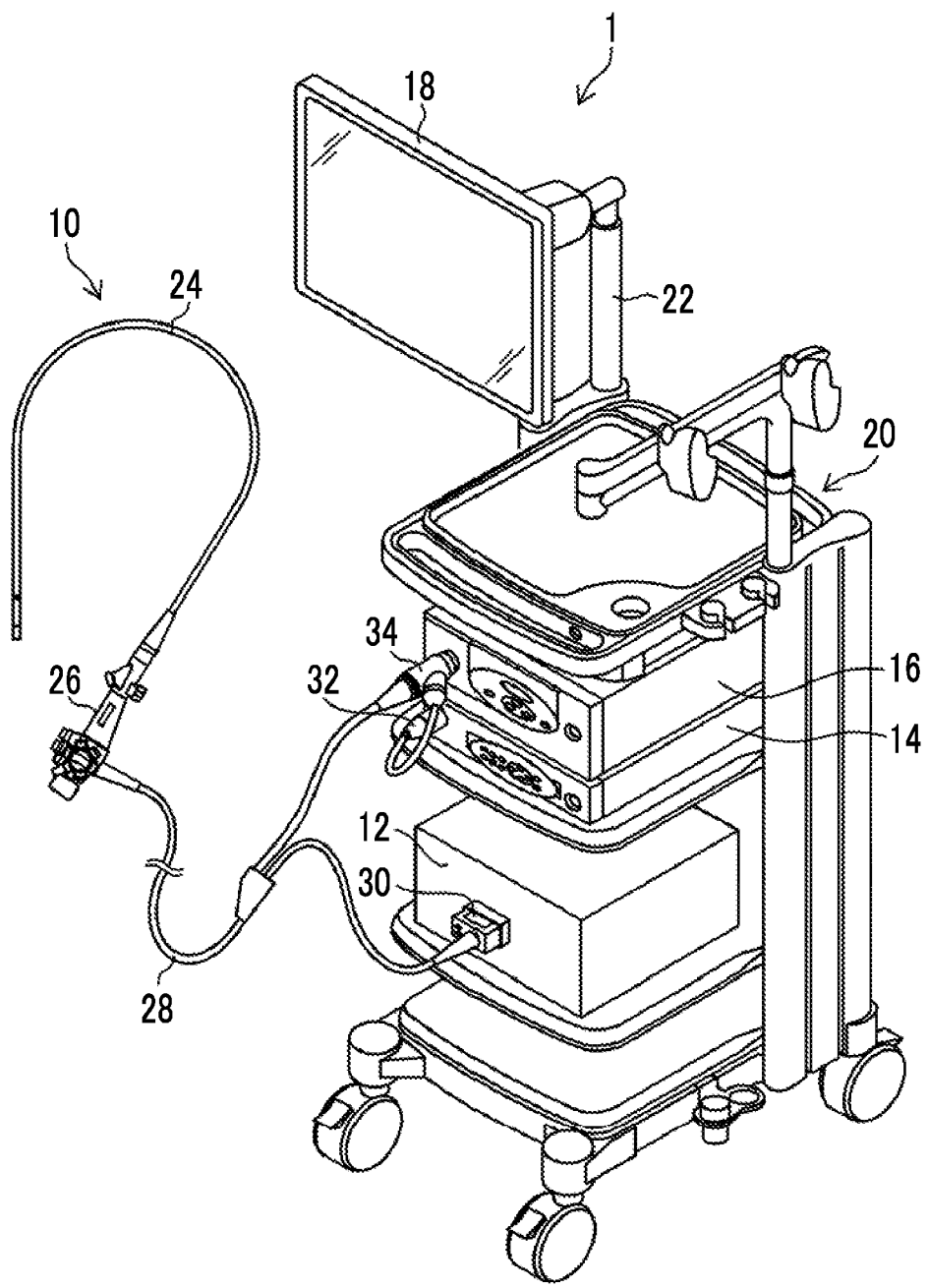
FIG. 1 is a diagram showing the appearance of an ultrasonography system including an endoscope according to a first embodiment.
Figure 2:
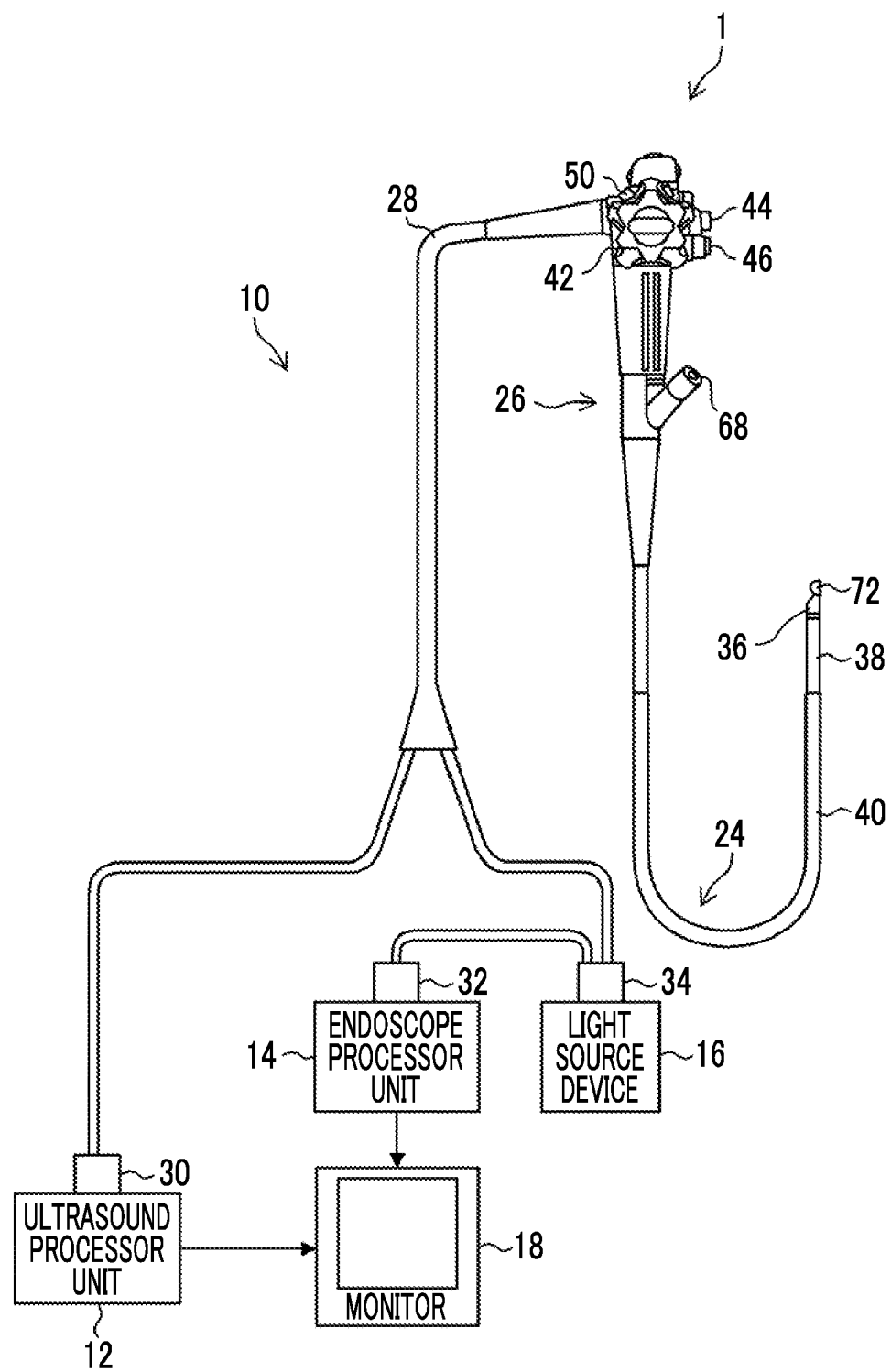
FIG. 2 is a schematic diagram showing the entire configuration of the ultrasonography system.

FIG. 1 is a diagram showing the appearance of an ultrasonography system 1 including an endoscope 10 according to a first embodiment. FIG. 2 is a schematic diagram showing the entire configuration of the ultrasonography system 1 shown in FIG. 1.

The ultrasonography system 1 includes an endoscope 10 that takes an endoscopic image and an ultrasound image of the inside of the body of an examinee, an ultrasound processor unit 12 that generates an ultrasound image, an endoscope processor unit 14 that generates an endoscopic image, a light source device 16 that supplies illumination light illuminating the inside of the body of the examinee to the endoscope 10, and a monitor 18 that displays the endoscopic image and the ultrasound image.

The ultrasound processor unit 12 transmits ultrasonic waves having a predetermined frequency to an object to be observed from the transmitting/receiving surfaces of a plurality of ultrasound transducers by driving the plurality of ultrasound transducers that form an ultrasound probe of the endoscope 10. Further, the ultrasound processor unit 12 acquires electrical signals (ultrasonic wave signals), which are to be obtained in a case in which ultrasonic waves reflected from the object to be observed are received by the transmitting/receiving surfaces, from the ultrasound probe, and generates video signals for the ultrasound image by performing various kinds of signal processing on the electrical signals. The ultrasound probe will be described later.

The endoscope processor unit 14 acquires imaging signals, which are to be transmitted from an imaging element disposed in the endoscope 10, by controlling the drive of the imaging element and generates video signals for the endoscopic image by performing various kinds of signal processing on the imaging signals.

The light source device 16 supplies illumination light to an illumination window to illuminate the observation field of view of the endoscope 10.

The monitor 18 receives the respective video signals, which are generated by the ultrasound processor unit 12 and the endoscope processor unit 14, and displays the ultrasound image and the endoscopic image. One of the ultrasound image and the endoscopic image may be displayed on the monitor 18, and both of the ultrasound image and the endoscopic image may be simultaneously displayed on the monitor 18.

Since the ultrasound processor unit 12, the endoscope processor unit 14, and the light source device 16 are mounted on a cart 20 with casters as shown in FIG. 1, the ultrasound processor unit 12, the endoscope processor unit 14, and the light source device 16 are integrally moved. Further, the monitor 18 is held on a post 22 of the cart 20. The direction and height of the screen of the monitor 18 are adjusted by a rotation mechanism (not shown) and a height adjustment mechanism (not shown) that are provided on the post 22.

Next, the endoscope 10 will be described.

A convex ultrasonic endoscope is exemplified as the endoscope 10 according to the first embodiment.

As shown in FIGS. 1 and 2, the endoscope 10 according to the first embodiment includes at least an insertion part 24 that is to be inserted into the body of an examinee, an operation unit 26 that is connected to the proximal end of the insertion part 24, and a universal cord 28 of which the proximal end is connected to the operation unit 26. A connector 30 to be connected to the ultrasound processor unit 12, a connector 32 to be connected to the endoscope processor unit 14, and a connector 34 to be connected to the light source device 16 are provided at the distal end of the universal cord 28. The endoscope 10 is attachably and detachably connected to the ultrasound processor unit 12, the endoscope processor unit 14, and the light source device 16 through these connectors 30, 32, and 34.

As shown in FIG. 2, the insertion part 24 includes a distal-end-portion body 36, a bendable portion 38, and a soft portion 40 in this order from the distal end side. The distal-end-portion body 36 is composed of a hard member in a substantially cylindrical shape. The bendable portion 38 is connected to the proximal end side of the distal-end-portion body 36. The soft portion 40 connects the proximal end side of the bendable portion 38 to the distal end side of the operation unit 26, has a small diameter and a long length, and has flexibility. The endoscope 10 according to the first embodiment includes an ultrasound probe 72 that is provided on the distal end side of the distal-end-portion body 36. The operation unit 26 includes an angle knob 42 that is operated to vertically and laterally bend the bendable portion 38 of the insertion part 24, a suction button 44 that is used to perform a suction operation, an air/water supply button 46 that is used to perform an air/water supply operation, and a standing lever 50 that is operated to rotationally move a standing base 48 (see FIGS. 3 and 4 to be described later). Further, a treatment tool insertion opening 68 through which various treatment tools (not shown) are inserted into a treatment tool channel is provided on the distal end side of the operation unit 26 so as to protrude.

Figure 3:
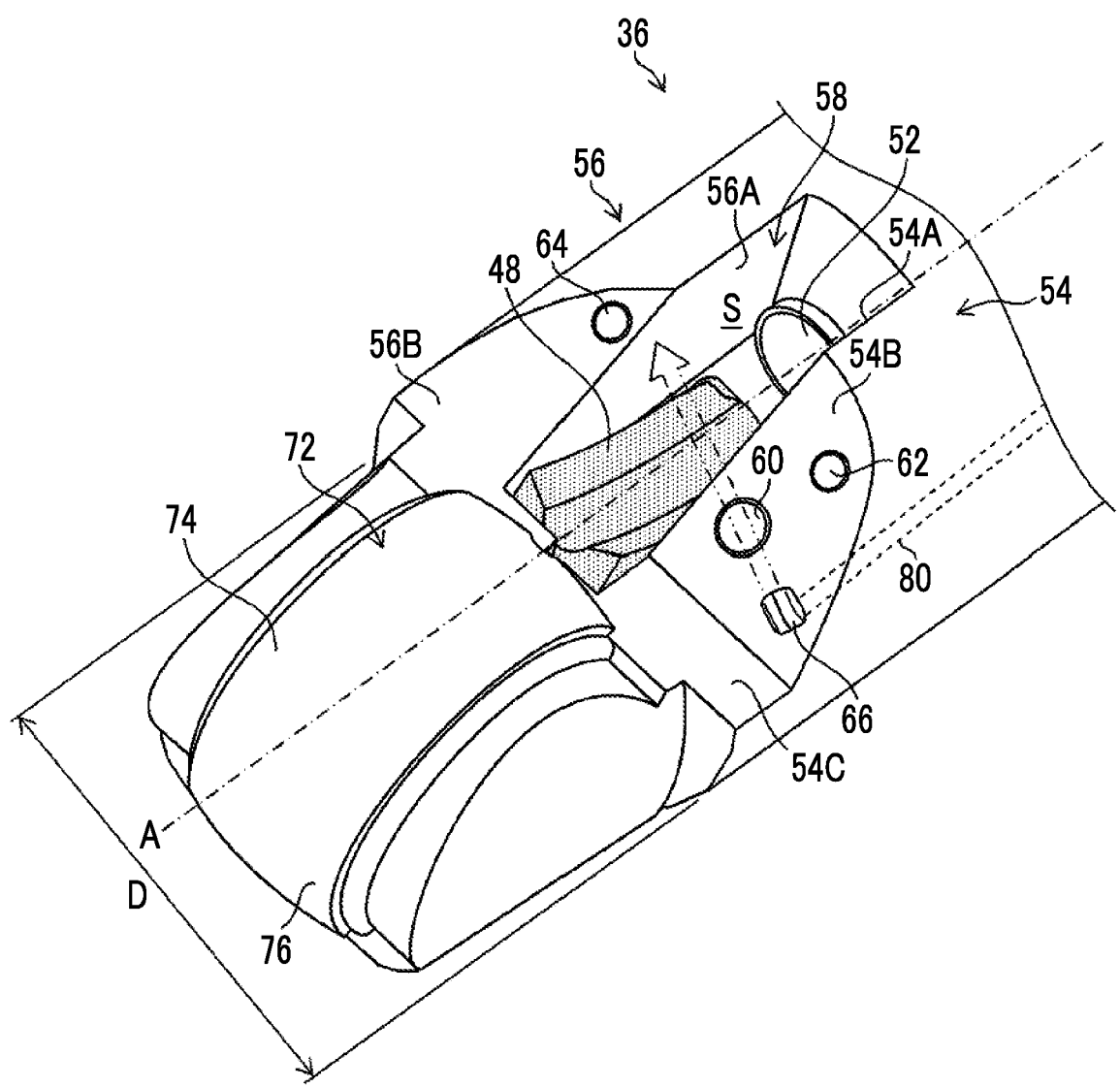
FIG. 3 is an enlarged perspective view of main portions of a distal-end-portion body of the endoscope in a state in which a standing base is in a falling position.
Figure 4:
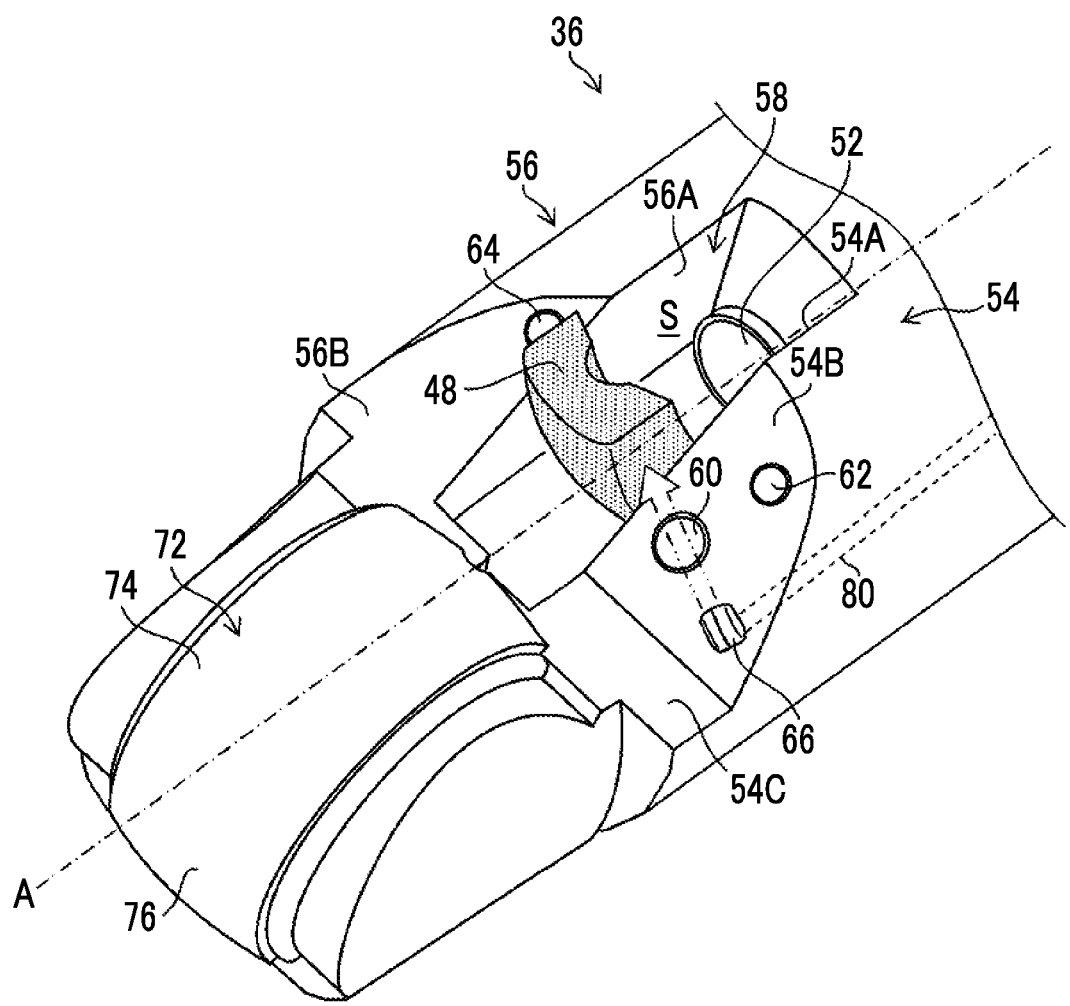
FIG. 4 is an enlarged perspective view of main portions of the distal-end-portion body of the endoscope in a state in which the standing base is in a standing position.
Figure 5:
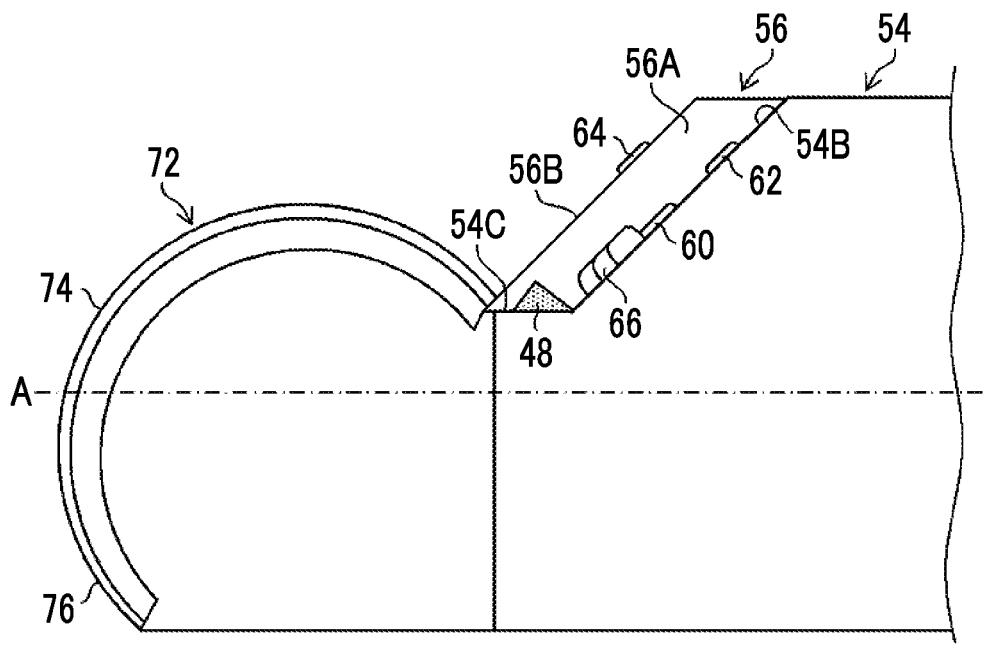
FIG. 5 is an enlarged side view of main portions of the distal-end-portion body of the endoscope shown in FIG. 3.

FIG. 3 is an enlarged perspective view of main portions showing the structure of the distal-end-portion body 36 in a state in which the standing base is in a falling position, and FIG. 4 is an enlarged perspective view of main portions showing the structure of the distal-end-portion body 36 in a state in which the standing base is in a standing position. FIG. 5 is a side view of the distal-end-portion body 36 in a state in which the standing base in the falling position.

In the first embodiment, an axial direction A of the distal-end-portion body 36 corresponds to the central axis of the insertion part 24 (see FIG. 1) in a longitudinal direction. The axial direction A of the distal-end-portion body 36 does not necessarily need to correspond to the central axis of the insertion part 24 in the longitudinal direction. For example, the axial direction A of the distal-end-portion body 36 may be parallel to the central axis of the insertion part 24 in the longitudinal direction and may be shifted in a direction orthogonal to the central axis of the insertion part 24.

As shown in FIG. 3, the distal-end-portion body 36 includes a treatment tool outlet 52 that is provided on the proximal end side thereof. The standing base 48 is disposed on the front side of the treatment tool outlet 52 so as to be spaced apart from the treatment tool outlet 52. The front side of the treatment tool outlet 52 means a position closer to the distal end than the treatment tool outlet 52. The standing base 48 may be disposed in the treatment tool outlet 52. The standing base 48 is rotationally moved between the standing position and the falling position by the operation of the standing lever 50. A space S is formed by a pair of walls 54 and 56 that includes wall surfaces 54A and 56A facing each other and is disposed so as to be spaced apart from each other. The standing base 48 is housed in the space S. An opening 58 is formed in the space S, and the space S is opened toward the ultrasound probe 72 in a case in which the distal-end-portion body 36 is viewed from the distal end side. In FIG. 3, the standing base 48 is in a state in which the standing base 48 is in the falling position.

In a case in which the standing base 48 is rotationally moved by the operation of the standing lever 50, the standing base 48 can be in a state in which the standing base 48 is the standing position as shown in FIG. 4.

A treatment tool (not shown) inserted from the treatment tool insertion opening 68 of the operation unit 26 is led out from the treatment tool outlet 52. The treatment tool passes through the space S, is led out from the opening 58, and is inserted into the body of an examinee. The lead-out direction of the treatment tool is changed by the standing base 48.

The treatment tool is not particularly limited, and a puncture needle and the like can be used as the treatment tool.

In the first embodiment, one wall 54 of the pair of walls 54 and 56 is provided with a flat surface 54B that is continuously connected to the wall surface 54A. Further, the other wall 56 of the pair of walls 54 and 56 is provided with a flat surface 56B that is continuously connected to the wall surface 56A.

The flat surface 54B of the wall 54 and the flat surface 56B of the wall 56 are inclined with respect to the axial direction A of the distal-end-portion body 36. An observation window 60, an illumination window 62, and a nozzle 66, which ejects washing water to the observation window 60, are disposed on the flat surface 54B. The nozzle 66 is disposed at a position on one side of the observation window 60 opposite to the space S. An illumination window 64 is disposed on the flat surface 56B of the other wall 56. The nozzle 66 is disposed closer to the outer periphery of the distal-end-portion body 36 than the observation window 60 in a case in which the nozzle 66 and the observation window 60 are viewed in the axial direction A. An air/water supply pipe line 80, which forms a fluid pipe line, is connected to the nozzle 66. Washing water and gas are supplied to the nozzle 66 through the air/water supply pipe line 80. The nozzle 66 ejects supplied washing water in the direction in which the observation window 60 and the other wall 56 are provided. The fact that the nozzle 66 is disposed closer to the outer periphery than the observation window 60 means that the nozzle 66 is positioned close to the outer periphery in a case in which the nozzle 66 and the observation window 60 are viewed in an ejection direction of washing water.

The wall 54 includes a flat surface 54C. The flat surface 54C is continuously connected to the flat surface 54B, extends toward the distal end side, and is substantially parallel to the axial direction A of the distal-end-portion body 36.

As long as the pair of walls 54 and 56 can form the space S that can house the standing base 48, the pair of walls 54 and 56 may be connected to each other on the proximal end side of the distal-end-portion body 36 as shown in FIG. 3.

Either washing water or gas is ejected toward the observation window 60 from the nozzle 66 by the operation of the air/water supply button 46 of the operation unit 26.

In the first embodiment, as shown in FIGS. 3 and 4, on the flat surface 54B, the nozzle 66 is disposed on the distal end side of the distal-end-portion body 36 and the observation window 60 is disposed closer to the proximal end than the nozzle 66. In a case in which the flat surface 54B is defined as the higher side while the flat surface 54C is used as a reference, the nozzle 66 is positioned on the lower side of the observation window 60. Washing water is ejected toward the observation window 60 from the nozzle 66, that is, toward the upper side from the lower side, and toward the center of the distal-end-portion body 36 from the outer periphery in a case in which the distal-end-portion body 36 is viewed in the axial direction A. The nozzle 66 and the observation window 60 may be set to the same height from the flat surface 54C used as a reference, and the nozzle 66 and the observation window 60 may be disposed at positions where the ejection direction of washing water to be ejected from the nozzle 66 is substantially orthogonal to the axial direction A.

In a case in which a reduction in the diameter D of the endoscope is considered, it is more preferable that the nozzle 66 is disposed below the observation window 60. Since the flat surface 54B can be effectively used in a case in which the nozzle 66 and the observation window 60 are disposed in this way, an increase in the size of the flat surface 54B can be suppressed.

As shown in FIG. 5, in the first embodiment, the wall surface 56A of the other wall 56 of the pair of walls 54 and 56 is formed so as to be longer than the wall surface 54A of one wall 54 and the distal end of the wall surface 56A of the other wall 56 is disposed closer to the distal end side of the distal-end-portion body 36 than the distal end of the wall surface 54A of one wall 54, in the axial direction A of the distal-end-portion body 36. The fact that the wall surface 56A of the other wall 56 is longer than the wall surface 54A of one wall 54 means that a ridge between the wall surface 54A and the flat surface 54B is positioned closer to the proximal end of the distal-end-portion body 36 than a ridge between the wall surface 56A and the flat surface 56B. Accordingly, in a case in which the distal-end-portion body 36 is viewed from one wall 54 in a direction orthogonal to the axial direction A, a part of the wall surface 56A of the other wall 56 can be visually recognized beyond the wall 54.

Therefore, the distal-end-portion body 36 is adapted so that the wall surface 56A of the other wall 56 of the pair of walls 54 and 56 is positioned on the extension of the ejection direction of washing water to be ejected from the nozzle 66.

In the first embodiment, the ejection direction of washing water to be ejected from the nozzle 66 is a direction crossing the axial direction A of the distal-end-portion body 36 as shown in FIG. 3. Crossing includes a case in which the ejection direction of washing water and the axial direction A cross each other in three dimensions and means that the ejection direction is not parallel to the axial direction A. Accordingly, washing water to be ejected from the nozzle 66 is ejected in a direction traversing the space S, which houses the standing base 48, after washing and passing the observation window 60.

An observation optical system (not shown) including the observation window 60 receives light, which is reflected from a subject present in the observation field of view, from the observation window 60, and includes an optical system member (not shown) that forms a subject image in the distal-end-portion body 36. An imaging element (not shown), which takes the subject image formed by the optical system member and generates an imaging signal, is disposed in the distal-end-portion body 36.

An illumination optical system (not shown) including the illumination windows 62 and 64 includes an optical system member that emits illumination light, which is transmitted from the light source device 16 (see FIG. 2) through a light guide (not shown), to the observation field of view through the illumination windows 62 and 64.

Next, the ultrasound probe 72 will be described. As shown in FIGS. 3 to 5, the ultrasound probe 72 is provided on the distal end side of the distal-end-portion body 36. The ultrasound probe 72 includes a curved surface 74 that is curved outward in a convex shape toward the distal end side from the proximal end side of the ultrasound probe 72. The curved surface 74 forms the outer surface of an acoustic lens 76. The ultrasound probe 72 includes a plurality of ultrasound transducers (not shown) that transmit and receive ultrasonic waves, and the plurality of ultrasound transducers are arranged in an arc shape along the outer surface of the acoustic lens 76 on the inside of the acoustic lens 76. Further, an ultrasound image (tomographic image) can be acquired by the ultrasound probe 72.

Next, the action of the structure will be described. As shown in FIG. 3, washing water is ejected toward the observation window 60 from the nozzle 66 provided on the flat surface 54B as shown by an arrow by the operation of the air/water supply button 46 of the operation unit 26. The observation window 60 and the nozzle 66 are disposed on the flat surface 54B in advance so that the observation window 60 and the space S are positioned on the extension of the ejection direction of washing water. The surface of the observation window 60 is washed with washing water. Washing water having passed the observation window 60 goes toward the space S that is positioned on the extension of the ejection direction. In the first embodiment, the wall surface 56A of the other wall 56 is positioned on the extension of the ejection direction of washing water to be ejected from the nozzle 66. Washing water, which has gone beyond the space S, collides with the wall surface 56A that is positioned on the extension of the ejection direction of washing water. Washing water, which has collided with the wall surface 56A, is guided in the direction of the standing base 48 housed in the space S. Washing water is guided to the side surface of the standing base 48 facing the wall surface 56A. The side surface of the standing base 48 can be washed with washing water. Since washing water is made to collide with the wall surface 56A, washing water can be efficiently guided toward the standing base 48.

Further, it is preferable that the side surface of the standing base 48 is positioned on the extension of the ejection direction of washing water to be ejected from the nozzle 66 in a state in which the standing base 48 is in the standing position as shown in FIG. 4. As shown in FIG. 4, washing water is ejected toward the observation window 60 from the nozzle 66 provided on the flat surface 54B as shown by an arrow by the operation of the air/water supply button 46 of the operation unit 26. The surface of the observation window 60 is washed with washing water, and washing water having passed the observation window 60 collides with the side surface of the standing base 48 that is positioned on the extension of the ejection direction of washing water and faces the wall surface 54A. The side surface of the standing base 48 facing the wall surface 54A can be washed with washing water. In the first embodiment, both side surfaces of the standing base 48 can be washed.

Since the standing base 48 is washed with washing water washing the observation window 60, the distal-end-portion body 36 does not need to be provided with a nozzle that is exclusively used to wash the standing base 48.

Washing water, which flows into the space S, is sucked from the treatment tool outlet 52 by the operation of the suction button 44 of the operation unit 26 and is removed from the space S.

Second Embodiment

An endoscope according to a second embodiment will be described with reference to FIG. 6. There is a case where the same components as the components of the endoscope according to the first embodiment are denoted by the same reference numerals as the reference numerals of the first embodiment and the description thereof are omitted.

Figure 6:
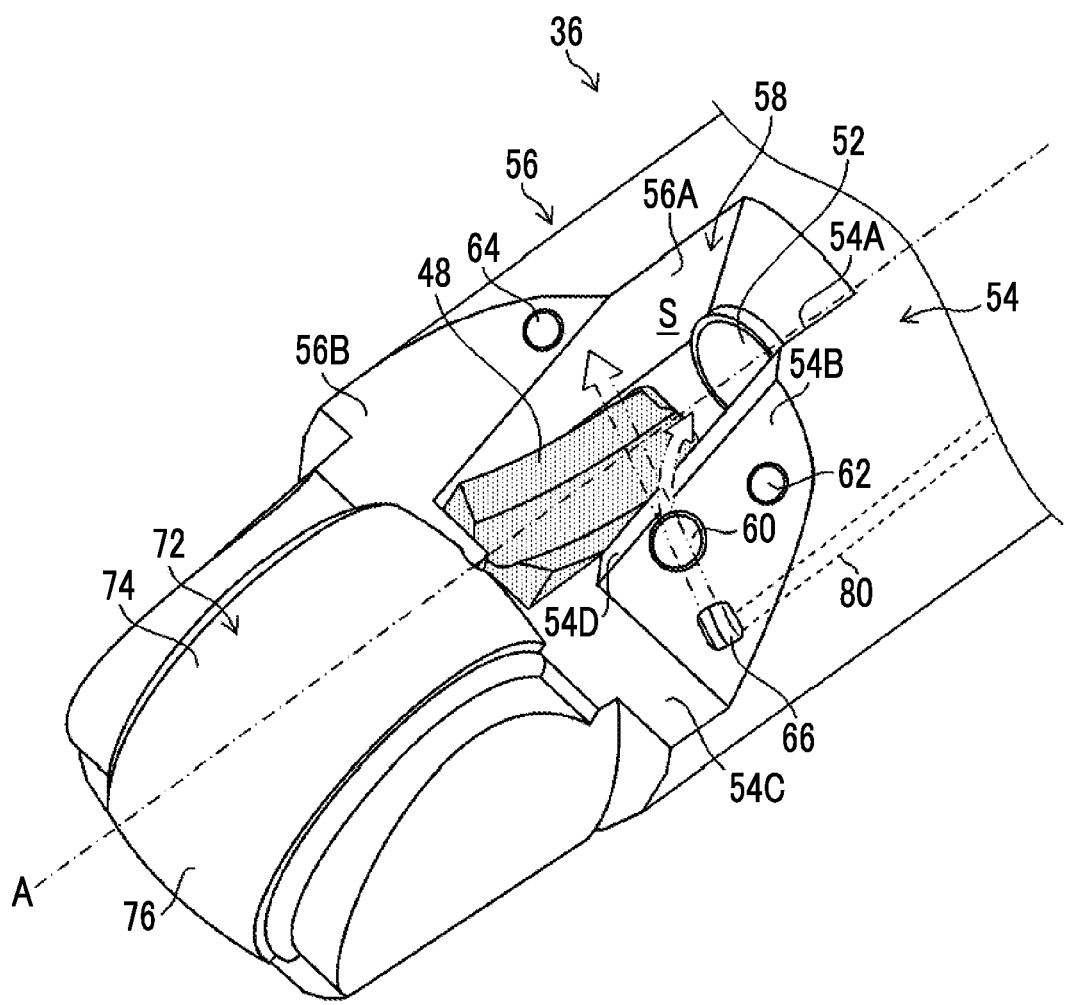
FIG. 6 is an enlarged perspective view of main portions of a distal-end-portion body of an endoscope in a state in which a standing base is in a falling position.

FIG. 6 is an enlarged perspective view of main portions showing the structure of a distal-end-portion body 36 of which a standing base 48 is in a falling position. A distal-end-portion body 36 includes a treatment tool outlet 52, a standing base 48 that is disposed in the treatment tool outlet 52, a pair of walls 54 and 56 that includes wall surfaces 54A and 56A forming a space S housing the standing base 48 and facing each other, an observation window 60 and an illumination window 62 that are disposed on a flat surface 54B of one wall 54, a nozzle 66 that is provided on the flat surface 54B on one side of the observation window 60 opposite to the space S and ejects washing water to the observation window 60, and an illumination window 64 that is disposed on a flat surface 56B of the other wall 56. The standing base 48 may be disposed on the front side of the treatment tool outlet 52 so as to be spaced apart from the treatment tool outlet 52. The flat surface 54B of the wall 54 and the flat surface 56B of the wall 56 are inclined with respect to an axial direction A of the distal-end-portion body 36.

Even in the second embodiment, the wall surface 56A of the other wall 56 of the pair of walls 54 and 56 is formed so as to be longer than the wall surface 54A of one wall 54 in the axial direction A of the distal-end-portion body 36. Accordingly, the wall surface 56A of the other wall 56 is positioned on the extension of the ejection direction of washing water to be ejected from the nozzle 66.

In the second embodiment, the wall 54 includes an inclined surface 54D that is continuously connected to the flat surface 54B and faces the space S from the flat surface 54B.

Next, the action of the structure will be described. As shown in FIG. 6, washing water is ejected toward the observation window 60 from the nozzle 66 provided on the flat surface 54B as shown by an arrow by the operation of the air/water supply button 46 of the operation unit 26. The surface of the observation window 60 is washed with washing water. A part of washing water having passed the observation window 60 is guided to the inclined surface 54D and is guided to the side surface of the standing base 48 facing the wall surface 54A. Further, the rest of the washing water having passed the observation window 60 goes beyond the space S and collides with the wall surface 56A of the other wall 56. As in the first embodiment, washing water is guided in the direction of the standing base 48 housed in the space S. Washing water collided with the wall surface 56A is guided to the side surface of the standing base 48 facing the wall surface 56A. In the second embodiment, both side surfaces of the standing base 48 can be washed with washing water even in a state in which the standing base 48 is in the falling position.

The inclined surface 54D has been exemplified, but a groove or the like may be formed as long as washing water can be guided to the side surface of the standing base 48 facing the wall surface 54A.

Washing water, which flows into the space S, is sucked from the treatment tool outlet 52 by the operation of the suction button 44 of the operation unit 26 and is removed from the space S.

Third Embodiment

An endoscope according to a third embodiment will be described with reference to FIG. 7. There is a case where the same components as the components of the endoscopes according to the first and second embodiments are denoted by the same reference numerals as the reference numerals of the first and second embodiments and the description thereof are omitted.

Figure 7:
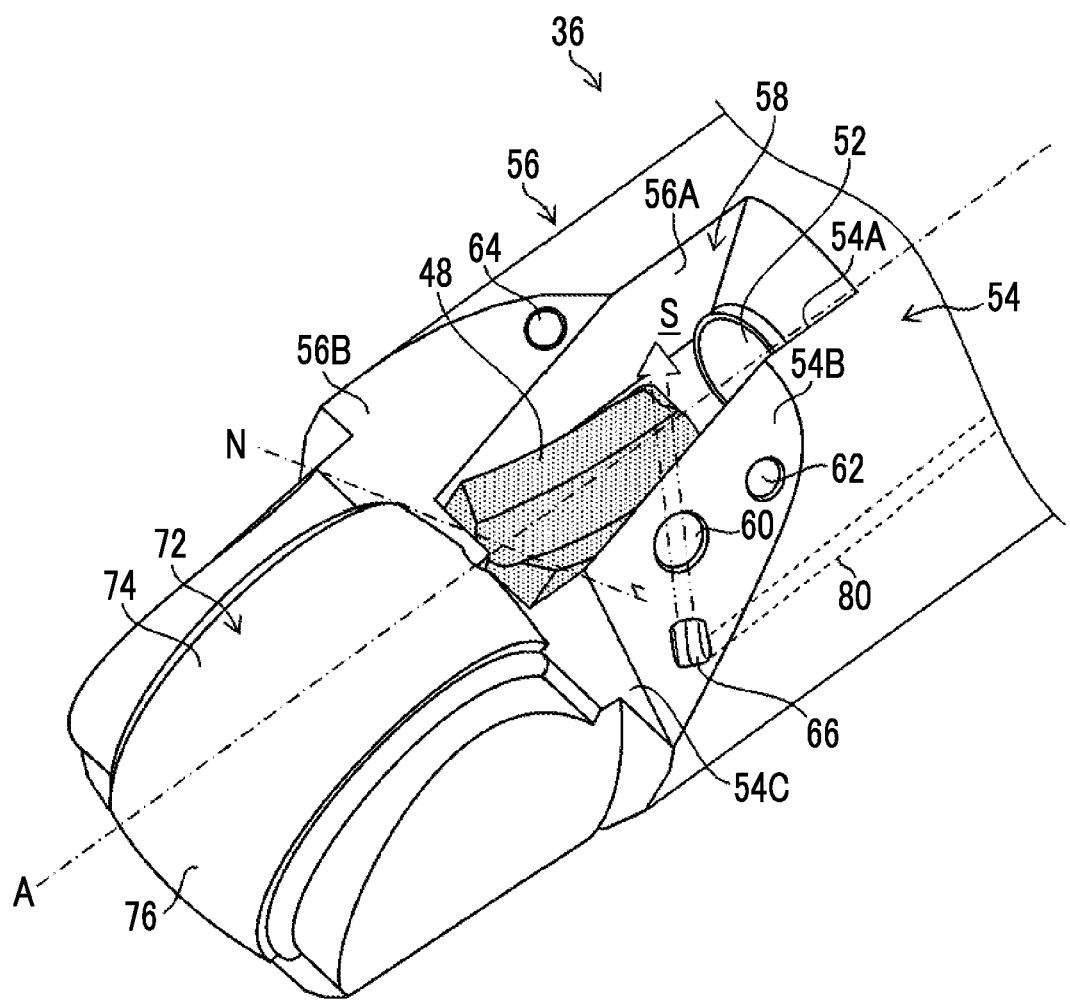
FIG. 7 is an enlarged perspective view of main portions of a distal-end-portion body of an endoscope in a state in which a standing base is in a falling position.

FIG. 7 is an enlarged perspective view of main portions showing the structure of a distal-end-portion body 36 of which a standing base 48 is in a falling position. A distal-end-portion body 36 includes a treatment tool outlet 52, a standing base 48 that is disposed in the treatment tool outlet 52, a pair of walls 54 and 56 that includes wall surfaces 54A and 56A forming a space S housing the standing base 48 and facing each other, an observation window 60 and an illumination window 62 that are disposed on a flat surface 54B of one wall 54, a nozzle 66 that is provided on the flat surface 54B on one side of the observation window 60 opposite to the space S and ejects washing water to the observation window 60, and an illumination window 64 that is disposed on a flat surface 56B of the other wall 56. The standing base 48 may be disposed on the front side of the treatment tool outlet 52 so as to be spaced apart from the treatment tool outlet 52. The flat surface 54B of the wall 54 and the flat surface 56B of the wall 56 are inclined with respect to an axial direction A of the distal-end-portion body 36.

In the third embodiment, the wall surface 56A of the other wall 56 of the pair of walls 54 and 56 and the wall surface 54A of one wall 54 are formed so as to have substantially the same length in the axial direction A of the distal-end-portion body 36. Accordingly, in a case in which the distal-end-portion body 36 is viewed from one wall 54, the wall surface 56A of the other wall 56 is not visually recognized due to the wall 54. Substantially the same length includes completely the same length and almost the same length.

As shown in FIG. 7, the flat surface 54B on which the observation window 60 and the nozzle 66 are disposed is inclined toward the space S as a whole. Since the flat surface 54B is inclined, the wall surface 56A of the other wall 56 is positioned on the extension of the ejection direction of washing water to be ejected from the nozzle 66. The inclination of the flat surface 54B toward the space S means that a normal direction N of the flat surface 54B is inclined toward the axial direction A.

Next, the action of the structure will be described. As shown in FIG. 7, washing water is ejected toward the observation window 60 from the nozzle 66 provided on the flat surface 54B as shown by an arrow by the operation of the air/water supply button 46 of the operation unit 26. The surface of the observation window 60 is washed with washing water. Washing water having passed the observation window 60 goes toward the space S that is positioned on the extension of the ejection direction. In the third embodiment, washing water, which has gone beyond the space S, collides with the wall surface 56A that is positioned on the extension of the ejection direction of washing water since the flat surface 54B is inclined. Washing water, which has collided with the wall surface 56A, is guided in the direction of the standing base 48 housed in the space S. Washing water is guided to the side surface of the standing base 48 facing the wall surface 56A. The side surface of the standing base 48 can be washed with washing water. Since washing water is made to collide with the wall surface 56A, washing water can be efficiently guided toward the standing base 48.

It is preferable that the side surface of the standing base 48 is positioned on the extension of the ejection direction of washing water to be ejected from the nozzle 66 in a state in which the standing base 48 is in the standing position. The side surface of the standing base 48, which is in the standing position, facing the wall surface 54A can be washed with washing water having passed the observation window 60. Both side surfaces of the standing base 48 can be washed in the third embodiment.

Washing water, which flows into the space S, is sucked from the treatment tool outlet 52 by the operation of the suction button 44 of the operation unit 26 and is removed from the space S.

Fourth Embodiment

An endoscope according to a fourth embodiment will be described with reference to FIG. 8. There is a case where the same components as the components of the endoscopes according to the first to third embodiments are denoted by the same reference numerals as the reference numerals of the first to third embodiments and the description thereof are omitted.

Figure 8:
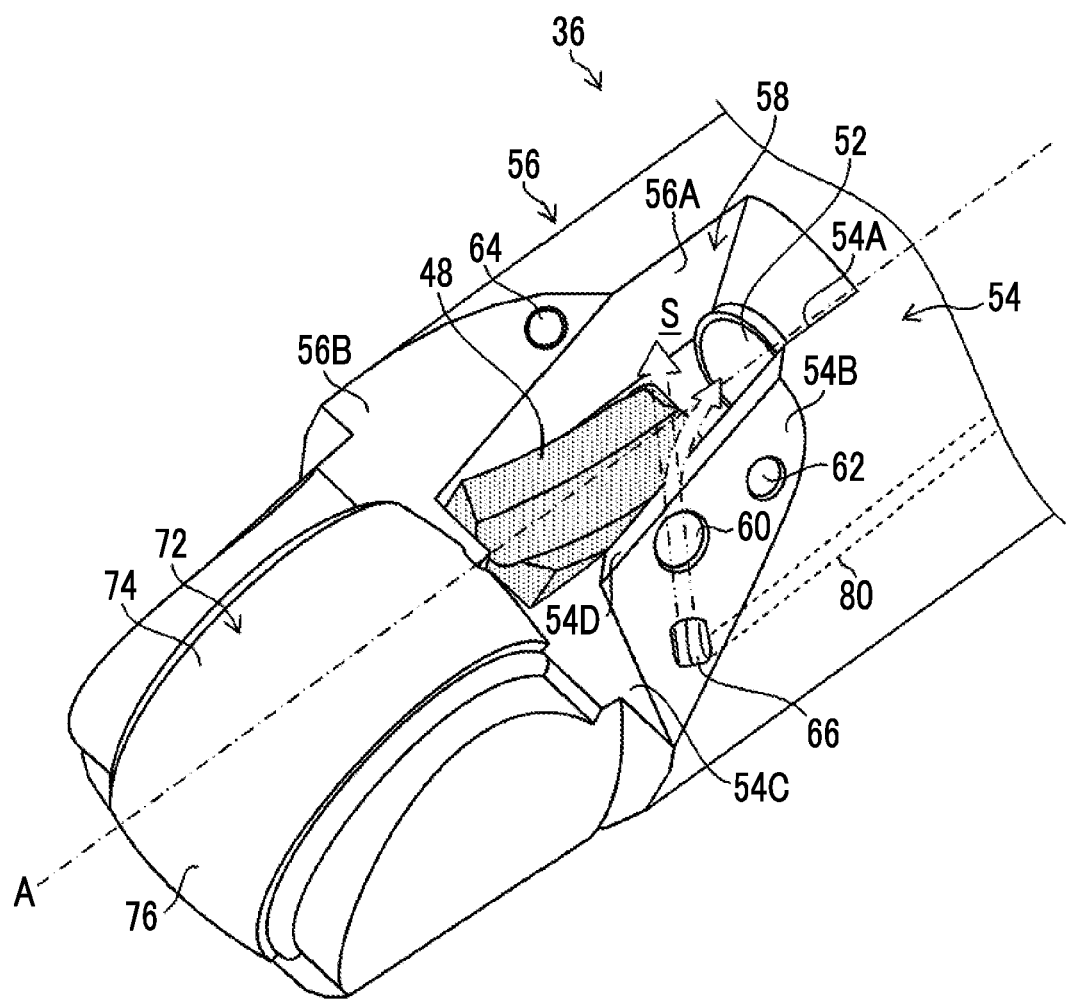
FIG. 8 is an enlarged perspective view of main portions of a distal-end-portion body of an endoscope in a state in which a standing base is in a falling position.

FIG. 8 is an enlarged perspective view of main portions showing the structure of a distal-end-portion body 36 of which a standing base 48 is in a falling position. A distal-end-portion body 36 includes a treatment tool outlet 52, a standing base 48 that is disposed in the treatment tool outlet 52, a pair of walls 54 and 56 that includes wall surfaces 54A and 56A forming a space S housing the standing base 48 and facing each other, an observation window 60 and an illumination window 62 that are disposed on a flat surface 54B of one wall 54, a nozzle 66 that is provided on the flat surface 54B on one side of the observation window 60 opposite to the space S and ejects washing water to the observation window 60, and an illumination window 64 that is disposed on a flat surface 56B of the other wall 56. The standing base 48 may be disposed on the front side of the treatment tool outlet 52 so as to be spaced apart from the treatment tool outlet 52. The flat surface 54B of the wall 54 and the flat surface 56B of the wall 56 are inclined with respect to an axial direction A of the distal-end-portion body 36.

As in the third embodiment, in the fourth embodiment, the wall surface 56A of the other wall 56 of the pair of walls 54 and 56 and the wall surface 54A of one wall 54 are formed so as to have substantially the same length in the axial direction A of the distal-end-portion body 36.

As shown in FIG. 8, the flat surface 54B on which the observation window 60 and the nozzle 66 are disposed is inclined toward the space S as a whole. Since the flat surface 54B is inclined, the wall surface 56A of the other wall 56 is positioned on the extension of the ejection direction of washing water to be ejected from the nozzle 66.

As in the second embodiment, in the fourth embodiment, the wall 54 includes an inclined surface 54D that is continuously connected to the flat surface 54B and faces the space S from the flat surface 54B.

Next, the action of the structure will be described. As shown in FIG. 8, washing water is ejected toward the observation window 60 from the nozzle 66 provided on the flat surface 54B as shown by an arrow by the operation of the air/water supply button 46 of the operation unit 26. The surface of the observation window 60 is washed with washing water. A part of washing water having passed the observation window 60 is guided to the inclined surface 54D and is guided to the side surface of the standing base 48 facing the wall surface 54A. Further, the rest of the washing water having passed the observation window 60 goes beyond the space S and collides with the wall surface 56A of the other wall 56. Washing water collided with the wall surface 56A is guided to the side surface of the standing base 48 facing the wall surface 56A. In the fourth embodiment, both side surfaces of the standing base 48 can be washed with washing water even in a state in which the standing base 48 is in the falling position.

The inclined surface 54D has been exemplified, but a groove or the like may be formed as long as washing water can be guided to the side surface of the standing base 48 facing the wall surface 54A.

Washing water, which flows into the space S, is sucked from the treatment tool outlet 52 by the operation of the suction button 44 of the operation unit 26 and is removed from the space S.

Fifth Embodiment

An endoscope according to a fifth embodiment will be described with reference to FIGS. 9 and 10. There is a case where the same components as the components of the endoscopes according to the first to fourth embodiments are denoted by the same reference numerals as the reference numerals of the first to fourth embodiments and the description thereof are omitted.

Figure 9:
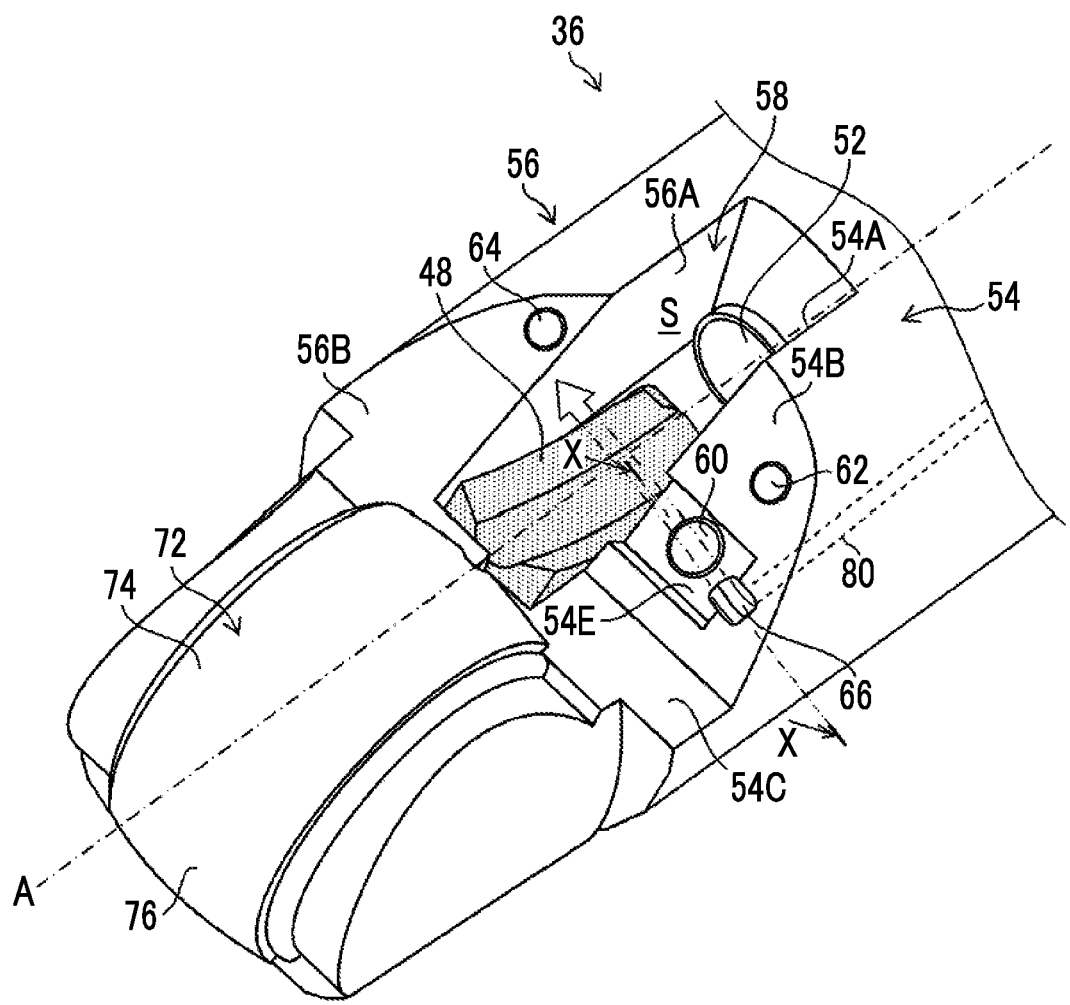
FIG. 9 is an enlarged perspective view of main portions of a distal-end-portion body of an endoscope in a state in which a standing base is in a falling position.

FIG. 9 is an enlarged perspective view of main portions showing the structure of a distal-end-portion body 36 of which a standing base 48 is in a falling position. A distal-end-portion body 36 includes a treatment tool outlet 52, a standing base 48 that is disposed in the treatment tool outlet 52, a pair of walls 54 and 56 that includes wall surfaces 54A and 56A forming a space S housing the standing base 48 and facing each other, an observation window 60 and an illumination window 62 that are disposed on a flat surface 54B of one wall 54, a nozzle 66 that is provided on the flat surface 54B on one side of the observation window 60 opposite to the space S and ejects washing water to the observation window 60, and an illumination window 64 that is disposed on a flat surface 56B of the other wall 56. The standing base 48 may be disposed on the front side of the treatment tool outlet 52 so as to be spaced apart from the treatment tool outlet 52. The flat surface 54B of the wall 54 and the flat surface 56B of the wall 56 are inclined with respect to an axial direction A of the distal-end-portion body 36. The flat surface 54B of the wall 54 and the flat surface 56B of the wall 56 are inclined with respect to an axial direction A of the distal-end-portion body 36. In the fifth embodiment, the flat surface 54B is provided with a recessed portion 54E and the observation window 60 is disposed in the recessed portion 54E. The recessed portion 54E is connected to the space S.

Figure 10:
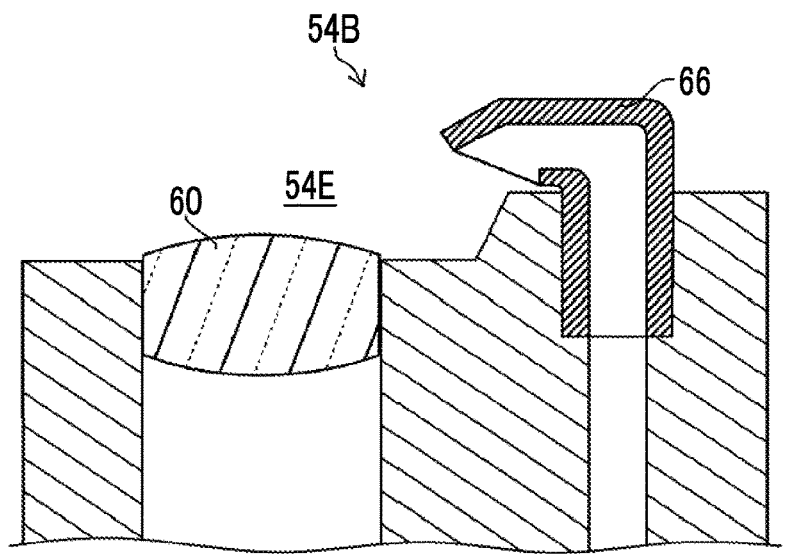
FIG. 10 is a cross-sectional view taken along line X-X of FIG. 9.

FIG. 10 is a cross-sectional view taken along line X-X of FIG. 9. As shown in FIG. 10, the observation window 60 is disposed in the recessed portion 54E of the flat surface 54B. Further, a stepped portion is formed between a surface of the flat surface 54B on which the observation window 60 is disposed and a surface of the flat surface 54B on which the nozzle 66 is disposed, and an inclined surface is formed on the stepped portion. At least an ejecting port of nozzle 66, to which the washing water is ejected is slightly inclined toward the recessed portion 54E so as to face the observation window 60.

In the fifth embodiment, the observation window 60 is disposed at a position lower than the nozzle 66. Washing water to be ejected from the nozzle 66 goes toward the observation window 60 along the inclined surface and the bottom of the recessed portion 54E. Since the recessed portion 54E is connected to the space S, washing water having passed the observation window 60 is ejected toward the wall surface 56A of the other wall 56. As a result, the wall surface 56A of the other wall 56 is positioned on the extension of the ejection direction of washing water to be ejected from the nozzle 66.

Next, the action of the structure will be described. As shown in FIG. 9, washing water is ejected toward the observation window 60 of the recessed portion 54E from the nozzle 66 provided on the flat surface 54B as shown by an arrow by the operation of the air/water supply button 46 of the operation unit 26. The surface of the observation window 60 is washed with washing water. Washing water having passed the observation window 60 goes along the recessed portion 54E and goes toward the space S that is positioned on the extension of the ejection direction. In the fifth embodiment, washing water, which has gone beyond the space S from the recessed portion 54E, collides with the wall surface 56A positioned on the extension of the ejection direction of washing water since the observation window 60 is provided in the recessed portion 54E. Washing water, which has collided with the wall surface 56A, is guided in the direction of the standing base 48 housed in the space S. Washing water is guided to the side surface of the standing base 48 facing the wall surface 56A. The side surface of the standing base 48 can be washed with washing water. Since washing water is made to collide with the wall surface 56A, washing water can be efficiently guided toward the standing base 48.

It is preferable that the side surface of the standing base 48 is positioned on the extension of the ejection direction of washing water to be ejected from the nozzle 66 in a state in which the standing base 48 is in the standing position. The side surface of the standing base 48, which is in the standing position, facing the wall surface 54A can be washed with washing water having passed the observation window 60. Both side surfaces of the standing base 48 can be washed in the fifth embodiment.

Washing water, which flows into the space S, is sucked from the treatment tool outlet 52 by the operation of the suction button 44 of the operation unit 26 and is removed from the space S.

Sixth Embodiment

An endoscope according to a sixth embodiment will be described with reference to FIG. 11. There is a case where the same components as the components of the endoscopes according to the first to fifth embodiments are denoted by the same reference numerals as the reference numerals of the first to fifth embodiments and the description thereof are omitted.

Figure 11:
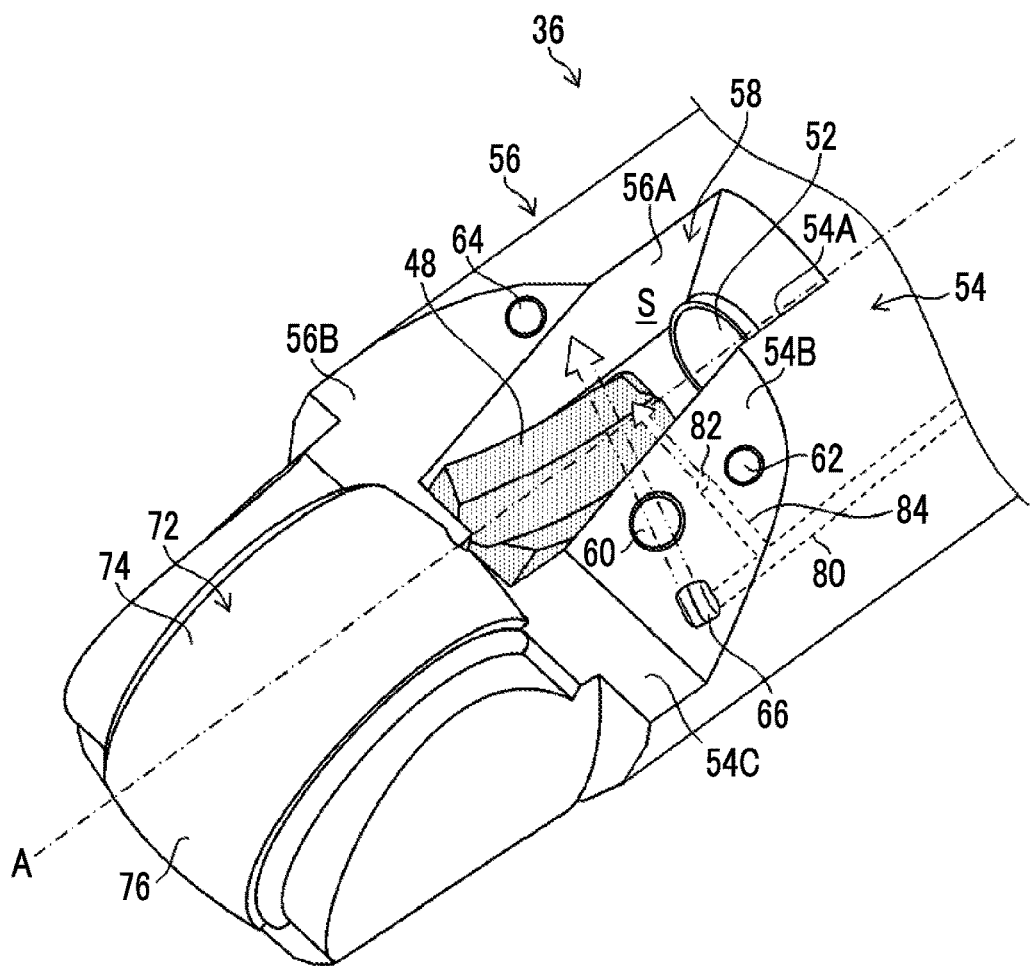
FIG. 11 is an enlarged perspective view of main portions of a distal-end-portion body of an endoscope in a state in which a standing base is in a falling position.

FIG. 11 is an enlarged perspective view of main portions showing the structure of a distal-end-portion body 36 of which a standing base 48 is in a falling position. A distal-end-portion body 36 includes a treatment tool outlet 52, a standing base 48 that is disposed in the treatment tool outlet 52, a pair of walls 54 and 56 that includes wall surfaces 54A and 56A forming a space S housing the standing base 48 and facing each other, an observation window 60 and an illumination window 62 that are disposed on a flat surface 54B of one wall 54, a nozzle 66 that is provided on the flat surface 54B on one side of the observation window 60 opposite to the space S and ejects washing water to the observation window 60, and an illumination window 64 that is disposed on a flat surface 56B of the other wall 56. The standing base 48 may be disposed on the front side of the treatment tool outlet 52 so as to be spaced apart from the treatment tool outlet 52. The flat surface 54B of the wall 54 and the flat surface 56B of the wall 56 are inclined with respect to an axial direction A of the distal-end-portion body 36.

Even in the sixth embodiment, the wall surface 56A of the other wall 56 of the pair of walls 54 and 56 is formed so as to be longer than the wall surface 54A of one wall 54 in the axial direction A of the distal-end-portion body 36. Accordingly, the wall surface 56A of the other wall 56 is positioned on the extension of the ejection direction of washing water to be ejected from the nozzle 66.

As shown in FIG. 11, the nozzle 66 is connected to an air/water supply pipe line 80. The wall surface 54A of one wall 54 is provided with a port 82 that ejects washing water. A branch pipe line 84, which connects the air/water supply pipe line 80 to the port 82, is provided.

The wall surface 54A is provided with the port 82 so that the wall surface 56A of the other wall 56 is positioned on the extension of the ejection direction of washing water to be ejected from the port 82 in a state in which the standing base 48 is in the falling position.

Next, the action of the structure will be described. As shown in FIG. 11, washing water is supplied to the air/water supply pipe line 80 by the operation of the air/water supply button 46 of the operation unit 26. A part of washing water, which is supplied to the air/water supply pipe line 80, is ejected from the port 82 through the branch pipe line 84. Washing water, which is ejected from the port 82, goes beyond the standing base 48 and collides with the wall surface 56A of the other wall 56. Washing water is guided in the direction of the standing base 48 housed in the space S, and is guided to the side surface of the standing base 48 facing the wall surface 56A.

The rest of the washing water is supplied to the nozzle 66. Washing water is ejected toward the observation window 60 from the nozzle 66 provided on the flat surface 54B as shown by an arrow. The surface of the observation window 60 is washed with washing water. Washing water having passed the observation window 60 goes toward the space S and collides with the wall surface 56A of the other wall 56. Washing water is guided in the direction of the standing base 48 housed in the space S. Washing water is guided to the side surface of the standing base 48 facing the wall surface 56A, and the side surface of the standing base 48 is washed. In the sixth embodiment, the standing base 48 can be more efficiently washed since washing water is directly ejected to the space S from the port 82 through the branch pipe line 84 that is branched from the air/water supply pipe line 80.

Further, it is preferable that the side surface of the standing base 48 is positioned on the extension of the ejection direction of washing water to be ejected from the nozzle 66 and the port 82 in a state in which the standing base 48 is in the standing position. The side surface of the standing base 48, which is in the standing position, facing the wall surface 54A can be washed with washing water having passed the observation window 60 and washing water to be ejected from the port 82. Both side surfaces of the standing base 48 can be washed in the sixth embodiment.

Washing water, which flows into the space S, is sucked from the treatment tool outlet 52 by the operation of the suction button 44 of the operation unit 26 and is removed from the space S.

The embodiments of the invention have been described on the basis of the first to sixth embodiments. However, the invention is not limited to these embodiments, and other combinations of the embodiments are allowed without departing from the invention.

EXPLANATION OF REFERENCES

1: ultrasonography system
10: endoscope
12: ultrasound processor unit
14: endoscope processor unit
16: light source device
18: monitor
20: cart
22: post
24: insertion part
26: operation unit
28: universal cord
30: connector
32: connector
34: connector
36: distal-end-portion body
38: bendable portion
40: soft portion
42: angle knob
44: suction button
46: air/water supply button
48: standing base
50: standing lever
52: treatment tool outlet
54: wall
54A: wall surface
54B: flat surface
54C: flat surface
54D: inclined surface
54E: recessed portion
56: wall
56A: wall surface
56B: flat surface
58: opening
60: observation window
62: illumination window
64: illumination window
66: nozzle
68: treatment tool insertion opening
72: ultrasound probe
74: curved surface
76: acoustic lens
80: air/water supply pipe line
82: port
84: branch pipe line A: axial direction
D: diameter
N: normal direction
S: space

What is claimed is:

1. An endoscope comprising:
an insertion part that includes a distal end and a proximal end;
a distal-end-portion body that is provided on a distal end side of the insertion part and formed with a treatment tool outlet from which a treatment tool is led out; and
an ultrasound transducer that is provided on a distal end side of the distal-end-portion body,
wherein the distal-end-portion body includes a pair of walls that includes wall surfaces facing each other, a standing base that is disposed in a space formed by the pair of walls and connected to the treatment tool outlet and that is rotationally moved between a standing position and a falling position, an observation window that is disposed on a flat surface inclined with respect to an axial direction of the distal-end-portion body on the distal end side of one wall of the pair of walls, a nozzle that is provided on the flat surface on one side of the observation window opposite to the space and ejects washing water to the observation window, and a fluid pipe line that is connected to the nozzle, and
wherein the wall surface of the other wall of the pair of walls is positioned on an extension of an ejection direction of the washing water to be ejected from the nozzle.

2. The endoscope according to claim 1,
wherein the ejection direction of the washing water to be ejected from the nozzle is a direction crossing the axial direction of the distal-end-portion body.

3. The endoscope according to claim 1,
wherein the nozzle is disposed on the distal end side of the distal-end-portion body, and
wherein the observation window is disposed closer to a proximal end of the distal-end-portion body than the nozzle.

4. The endoscope according to claim 2,
wherein the nozzle is disposed on the distal end side of the distal-end-portion body, and
wherein the observation window is disposed closer to a proximal end of the distal-end-portion body than the nozzle.

5. The endoscope according to claim 1,
wherein the nozzle is disposed closer to an outer periphery of the distal-end-portion body than the observation window.

6. The endoscope according to claim 2,
wherein the nozzle is disposed closer to an outer periphery of the distal-end-portion body than the observation window.

7. The endoscope according to claim 3,
wherein the nozzle is disposed closer to an outer periphery of the distal-end-portion body than the observation window.

8. The endoscope according to claim 4,
wherein the nozzle is disposed closer to an outer periphery of the distal-end-portion body than the observation window.

9. The endoscope according to claim 1,
wherein the wall surface of the other wall of the pair of walls is longer than the wall surface of the one wall in the axial direction of the distal-end-portion body, and
wherein a distal end of the wall surface of the other wall is disposed closer to the distal end side of the distal-end-portion body than a distal end of the wall surface of one wall.

10. The endoscope according to claim 2,
wherein the wall surface of the other wall of the pair of walls is longer than the wall surface of the one wall in the axial direction of the distal-end-portion body, and
wherein a distal end of the wall surface of the other wall is disposed closer to the distal end side of the distal-end-portion body than a distal end of the wall surface of one wall.

11. The endoscope according to claim 3,
wherein the wall surface of the other wall of the pair of walls is longer than the wall surface of the one wall in the axial direction of the distal-end-portion body, and
wherein a distal end of the wall surface of the other wall is disposed closer to the distal end side of the distal-end-portion body than a distal end of the wall surface of one wall.

12. The endoscope according to claim 4,
wherein the wall surface of the other wall of the pair of walls is longer than the wall surface of the one wall in the axial direction of the distal-end-portion body, and
wherein a distal end of the wall surface of the other wall is disposed closer to the distal end side of the distal-end-portion body than a distal end of the wall surface of one wall.

13. The endoscope according to claim 5,
wherein the wall surface of the other wall of the pair of walls is longer than the wall surface of the one wall in the axial direction of the distal-end-portion body, and
wherein a distal end of the wall surface of the other wall is disposed closer to the distal end side of the distal-end-portion body than a distal end of the wall surface of one wall.

14. The endoscope according to claim 6,
wherein the wall surface of the other wall of the pair of walls is longer than the wall surface of the one wall in the axial direction of the distal-end-portion body, and
wherein a distal end of the wall surface of the other wall is disposed closer to the distal end side of the distal-end-portion body than a distal end of the wall surface of one wall.

15. The endoscope according to claim 7,
wherein the wall surface of the other wall of the pair of walls is longer than the wall surface of the one wall in the axial direction of the distal-end-portion body, and
wherein a distal end of the wall surface of the other wall is disposed closer to the distal end side of the distal-end-portion body than a distal end of the wall surface of one wall.

16. The endoscope according to claim 1,
wherein the flat surface is inclined toward the space.

17. The endoscope according to claim 1,
wherein one wall includes an inclined surface inclining from the flat surface toward the space.

18. The endoscope according to claim 1,
wherein the observation window is disposed in a recessed portion provided on the flat surface.

19. The endoscope according to claim 1, further comprising:
a port that is provided on the wall surface of the one wall and ejects the washing water; and
a branch pipe line that connects the port to the fluid pipe line.

20. The endoscope according to claim 19,
wherein the wall surface of the other wall is positioned on an extension of the ejection direction of the washing water to be ejected from the port in a state in which the standing base is in the falling position.

\* \* \* \* \*